United States Patent [19]

Engelhardt et al.

[11] 3,966,829

[45] June 29, 1976

[54] METHOD OF PURIFYING MONOALCOHOLS

[75] Inventors: Friedrich Engelhardt, Hamburg; Karl Erhard, Buchholz; Gündolf Füchs, Steinbeck-Meilsen, all of Germany

[73] Assignee: Deutsche Texaco Aktiengesellschaft, Hamburg, Germany

[22] Filed: Sept. 27, 1974

[21] Appl. No.: 509,873

Related U.S. Application Data

[63] Continuation-in-part of Ser. No. 463,080, April 22, 1974, abandoned, which is a continuation of Ser. No. 873,739, Nov. 26, 1969, abandoned, which is a continuation of Ser. No. 638,742, May 16, 1967, abandoned.

[30] Foreign Application Priority Data

Sept. 24, 1966 Germany.......................... 1568415

[52] U.S. Cl. ...................... 260/643 B; 260/642 R; 260/643 F
[51] Int. Cl.² .......................................... C07C 29/24
[58] Field of Search......... 260/642 R, 643 F, 643 B, 260/642 E; 423/628

[56] References Cited

UNITED STATES PATENTS

| 2,086,713 | 7/1937 | Grun.............................. 260/642 R |
| 2,406,420 | 8/1946 | Weiser et al....................... 423/628 |
| 3,308,173 | 3/1967 | Emrick............................. 260/642 R |
| 3,461,176 | 8/1969 | Lundeer et al.................. 260/643 F |
| 3,468,965 | 9/1969 | Wikman et al.................. 260/642 R |

FOREIGN PATENTS OR APPLICATIONS

| 589,709 | 6/1947 | United Kingdom............. 260/642 R |
| 1,149,281 | 4/1969 | United Kingdom............. 260/642 R |

*Primary Examiner*—Joseph E. Evans
*Attorney, Agent, or Firm*—Burgess, Dinklage & Sprung

[57] ABSTRACT

A process for purifying a primary monoalcohol being admixed with diol impurities containing primary and secondary hydroxyl groups without appreciably affecting the primary hydroxyl groups of said admixture, which comprises passing a mixture of said diol and said monoalcohol at a temperature of about 170° to 220°C in the liquid phase over a gamma-alumina catalyst.

17 Claims, No Drawings

METHOD OF PURIFYING MONOALCOHOLS

CROSS REFERENCES TO RELATED APPLICATIONS

This is a continuation-in-part of co-pending application Ser. No. 463,080, filed Apr. 22, 1974, now abandoned which, in turn, is a continuation of Ser. No. 873,739, filed Nov. 26, 1969, now abandoned, which, in turn, is a continuation of Ser. No. 638,742, filed May 16, 1967, now abandoned.

BACKGROUND OF THE INVENTION

1. Field of the Invention

This invention relates to the selective dehydration of secondary hydroxyl groups in an aliphatic diol containing equal amounts of primary and secondary hydroxyl groups when such diol is in admixture with a great excess of aliphatic monoalcohol. More particularly, this invention is directed to the selective dehydration of the secondary hydroxyl groups in said monoalcohol and diol admixture and conversion of the unsaturated product so prepared to essentially pure monoalcohol by hydrogenation. This invention is particularly directed to the removal of diol impurities from primary monoalcohols whereby to improve the characteristics of such monoalcohols.

2. Discussion of the Prior Art

It is known that alcohols, particularly medium and long chain alcohols such as those containing about 4 carbon atoms, can be synthesized by several techniques including oxaldehyde synthesis coupled with reduction of the aldehyde group to an alcohol and Ziegler synthesis using an ethylene insertion type of reaction with an aluminum alkyl, preferably aluminum triethyl, followed by oxidation of the product to alcohol. Still further, it is known to produce relatively long and intermediate chain length alcohols by Aldol condensation and reduction.

Due to the mechanisms of synthesis, the alcohols synthesized as described above, inevitably contain amounts of by-products, among these particularly olefin and carbonyl compounds. Since synthetic monoalcohols having more than about 4 carbon atoms have recently gained increased importance in industry as intermediate or starting materials for the preparation of numerous products, as, for example, wetting agents and synthetic resins, it is often desirable to eliminate these by-products of synthesis. Thus, for example, it is known to remove such impurities by hydrogenation in the presence of suitable hydrogenation catalysts.

It has been found that using monoalcohols, particularly those obtained by the Ziegler process as intermediate or starting materials, difficulties arise even though the alcohol may have undergone such a purification step. It has been found that such alcohols often have presented difficulties owing to the presence of minor quantities of dihydric alcohols, e.g. diols. In other words, the pimary monoalcohols obtained inevitably contain a small amount of diols characterised by one primary and one secondary hydroxyl group. For simplicity, such diols will be denoted "secondary diols" hereinafter. These compounds are not converted during hydrogenation and remain in the monoalcohols as impurities. They steadfastly resist the purification method and seriously affect usability of the alcohols. Sulfaction of the mixture presents an objectionable odor due to sulfated diol.

It is known that alcohols can be selectively converted whereby to dehydrate secondary hydroxyl groups of diols when such diols are in admixture with primary monoalcohols. Thus, it was proposed according to U.S. Pat. No. 3,468,965 to Wikman et al to subject the mixture of primary monoalcohol and secondary diol to the action of a copper chromite catalyst and to maintain the mixture in the presence of such catalyst while under a hydrogen pressure of at least about 7 atmospheres. While such technique is useful to some extent in decreasing the diol concentration in a monoalcohol stream, such technique is expensive owing to the nature of the catalyst and to the pressures which need be employed on the reaction mixture. Additionally, such technique does not selectively dehydrate the secondary hydroxyl group in a commercially feasible manner, because too much of the primary monoalcohol is dehydrated along with the secondary hydroxyl group, thereby consuming valuable product.

It is an object of this invention, therefore, to provide a process for the removal of secondary hydroxyl groups from secondary diols when such diols are present in an alcohol stream comprising primary monoalcohol.

It is another object of this invention, therefore, to provide a process which can be carried out at atmospheric pressure or at only slightly elevated pressures with an inexpensive and readily available catalyst.

It is still a further object of this invention, therefor, to provide a process for the conversion of secondary diols to unsaturated monoalcohols wherein during such conversion, primary monoalcohols is admixture with such secondary diols are only negligibly dehydrated.

These and other objects of this invention will become more apparent in the following disclosure.

SUMMARY OF THE INVENTION

The objects of this invention are attained by a process for selectively converting a secondary diol in admixture with a primary monoalcohol wherein the secondary diol is converted to a primary monoalcohol without appreciably effecting dehydration of the monoalcohol in the feed. This desirable conversion is provided by passing a mixture of secondary diol and primary monoalcohol at a temperature of about 170° to 220°C over a γ-alumina catalyst, generally at a pressure up to 10 atm. absolute.

It has been found, in accordance with the present invention, that diols can be selectively converted to unsaturated monoalcohols while in the presence of monoalcohol feed in such a manner that the monoalcohol feed is only negligibly dehydrated. The diols which can be subjected to this treatment are generally diols having between 6 and 24 carbon atoms. Generally speaking, these diols are aliphatic diols, especially alkenediols. They are generally straight or branched chain diols and can have some degree of unsaturation in the aliphatic chain.

The monoalcoholic stream in which the diols are present are monoalcoholic streams of primary aliphatic alcohols, especially primary monoalcoholic aliphatic streams whose alcoholic component consists of a major amount of $C_8-C_{24}$ aliphatic primary monoalcohols.

Generally, speaking, the primary monoalcoholic stream in which the diol is present consists of a mixture of a number of different primary monoalcohols having aliphatic chain lengths between $C_8$ and $C_{24}$. For instance, a given percentate of the monoalcohol component can have a chain length of between $C_6$ and $C_{10}$ and an additional component of $C_{12}$–$C_{18}$. The diol can have as low as 4 carbon atoms in the chain and can be a mixture of various diols such as a diol mixture of diols of 4 to 6 carbon atoms, diols of 8 to 14 carbon atoms, diols of 8 to 14 carbon atoms and diols whose carbon atom content is at least 16 carbon atoms per molecule.

The process of the invention can be carried out at normal atmospheric pressure or at a pressure up to 10 atmospheres absolute. It can most advantageously be carried out at superatmospheric pressure less than 6.5 atmospheres absolute, especially 1 to 5 atmospheres absolute. Superatmospheric pressure is applied only in order to prevent evaporation of the $C_6$ alcohol. The diol removal is best at atmospheric pressure. In carrying out the process, it is desirable that the dehydration take place in the presence of hydrogen or nitrogen gas, especially when mild superatmospheric pressures are employed.

Generally speaking, the selective dehydration is carried out at a temperature between 170° and 220°C. The process can be carried out batch-wise or continuously. When the process is carried out continuously, a mixture of secondary diol and primary monoalcohol is passed continuously through a bed of catalyst at a liquid hourly space velocity of between 0.5 and 1.0.

Following conversion of the secondary diol to unsaturated primary monoalcohol, the mixture is generally subjected to hydrogenation, preferably in the presence of a hydrogenation catalyst. The purpose of such subsequent hydrogenation is to saturate the double bonds created during the dehydration reaction and existing already before the diol removal treatment.

When the process is carried out batch-wise, it is generally carried out such that the mixture of secondary diol and primary monoalcohol remains in contact with from 2 to 10wt.% of the γ-alumina catalyst for a period of time between 180 and 480 minutes, preferably between 240 and 300 minutes.

The invention will be more readily understood and its mode of practice more appreciated when reference is made to the following Examples:

EXAMPLE 1

An alcohol cut obtained by the Ziegler process and having a carbon number of $C_8$–$C_{18}$, a hydroxyl number of 296 and a diol content of 0.8%, which diols were a mixture of isomers containing OH groups, predominantly in the 1,2 and 1,3 position, was stirred in a vessel provided with an agitator and 2% by weight γ-alumina in powder form. The mixture was maintained in contact with the γ-alumina at 220°C for 6 hours. The diol content was thereby reduced to 0.05 weight percent. The material had a hydroxyl number of 290.

EXAMPLE 2

In a vertical reactor, a $C_{12/14}$ alcohol cut was passed over a stationary bed of γ-alumina catalyst at a space velocity of 0.5 volumes per volume of catalyst per hour. The alcohol cut was at a temperature of 190°C. The hydroxyl number of the treated product was 275. The diol content dropped from an initial value of about 1.0% to less than 0.05 weight percent.

EXAMPLE 3

The same apparatus as described in Example 2, $C_{12/14}$ alcohol cut, with the same initial properties, namely, a hydroxyl number of 283 and a diol content of 1.0 weight percent, was pumped through the column from below (sump-phase treatment) at 200°C with a space velocity of 1 volume/volume of catalyst/hour. The hydroxyl number of the treated product was 275. The treated product had a diol content of less than 0.05%. The high hydroxyl number of the product relative to the hydroxyl number of the starting material and the relatively negigible diol content of the resultant product showed that selective dehydration is occurring — selective in the sense that virtually only secondary hydroxyl groups are undergoing dehydration. If dehydration as a general phenomenon were observed, not only would the diol content drop, but the hydroxyl number would show a marked decrease.

EXAMPLE 4

By the method described above, an alcohol cut with a carbon number of $C_{12/14}$, an OH number of 286 and a diol content of 0.85% by weight was stirred with 2% γ-alumina in powder form at 220°C for 6 hours. After removal of the γ-alumina catalyst by filtration, there was obtained a product whose diol content had dropped to less than 0.05 %. The resultant product, however, had a hydroxyl number of 276, a bromine number of 0.79 mg bromine per 100 mg, and a CO number of 1100 ppm.

The material was thereafter subjected to hydrogenation employing a commerical nickel catalyst. The alcohol had the following properties:

| | |
|---|---|
| Diol content | 0.05% |
| Hydroxyl number | 276 |
| Bromine number | 0.1 mg Br/100 mg |
| CO number | 127 ppm |

The hydrogenation was performed at a temperature of 125°C, at hydrogen pressure of 18 kiloponds per square centimeter utilizing a space velocity of 2.5 volumes/volumes hour, using a hydrogenation catalyst which was commercially available under the trademark "Harshaw-Kontakt T 0104 Ni". It is believed that the material was about 52% by weight nickel on alumina.

It will be realized that the subsequent hydrogenation process can be carried out with a number of hydrogenation catalysts, particularly nickel-containing hydrogenation catalysts. Of those which are useful, the following should be mentioned: "Leuna-Kontakt 6540", "Doduco 731", "Ruhrchemie-Katalysator RCH 50/5", containing each 50 to 56% by weight nickel or alumina and/or kieselguhr. These have proved nearly equal in activity at temperatures in the range of 110°–130°C, at hydrogen pressure up to 20 kiloponds per square centimeter and at a space velocity of 1–4 volumes liquid per volume catalyst per hour. Generally speaking, the hydrogenation is carried out at a hydrogen pressure of between 15 and 20 kiloponds per square centimeter using a temperature of between 110° and 130°C, and the above recited space velocity.

The higher temperatures of the range and lower space velocity in the hydrogenation are more suited for hydrogenating the longer chained unsaturated alcohols having more than 14 carbon atoms in the chain.

In the dehydration process it is preferred to use, in a batch process, between 2 and 5 weight percent γ-alumina catalyst.

EXAMPLE 5

Several aliphatic alcohol preparations were prepared to evaluate the relative merits of γ-alumina as dehydration catalyst against other materials thus far proposed. The four synthetic alcohol preparations are known as Alfol A, B, C and D.

Alfol A was 1,12-octadecane diol prepared by hydrogenating technical 12-hydroxy stearic acid octyl ester. The material had a hydroxyl number of 383 and a bromine number of 3.0.

Alfol B was a $C_{12}$–$C_{18}$ blend of aliphatic alcohols comprising 51.3 weight percent $C_{12}$ aliphatic alcohol, 25 weight percent $C_{14}$ aliphatic alcohol, 16 weight percent $C_{16}$ aliphatic alcohol, 5 weight percent $C_{18}$ aliphatic alcohol, 1.2 weight percent of a diol mixture and 1.5 weight percent of nonalcoholic components, mainly paraffins and olefins. The material was obtained by distillation of a commercial (Condea) $C_{6+}$ crude alcohol. The material had a diol content of 1.2 weight percent, a hydroxyl number of 275, and a bromine number of 0.4.

Alfol C was a blend of $C_{12}$–$C_{16}$ alcohols obtained by fractional distillation of Condea $C_{6+}$ crude alcohol. $C_{12}$, $C_{14}$ and $C_{16}$ cuts were obtaind from the fractional distillation and blended at a ratio of 65:25:10 according to Example 1 of U.S. Pat. No. 3,468,965. The material had a hydroxyl number of 284 and a diol content of 0.8 weight percent.

Alfol D was also obtained from a commercial $C_{6+}$ crude (Condea). It had the following composition:

| | |
|---|---|
| Primary Straight-Chained $C_6$—$C_{12}$ Monoalcohols | 49–50 weight percent |
| Primary Straight-Chained $C_{12}$–$C_{18}$ Monoalcohols | 38.5–39 weight percent |
| Primary Straight-Chained Monoalcohols having at least 20 carbon atoms per molecule | 8–8.5 weight percent |
| Diols having 4 to 6 carbon atoms per molecule | About 0.08 weight percent |
| Diols having 8 to 14 carbon atoms per molecule | About 0.35 weight percent |
| Diols having at least 16 carbon atoms per molecule | About 0.07 weight percent |

The total diol content was about 0.5 weight percent. The diols having 8 to 14 carbon atoms had the following composition:

| | |
|---|---|
| 14.0 weight percent | 1,2-diols |
| 82.5 weight percent | 1,3-diols |
| 2.5 weight percent | 1,4-diols |
| 1.0 weight percent | 1,5-diols and others |

The hydroxyl number of Alfol D was 330 and its diol content was 0.5 weight percent.

There were obtained three catalysts as follows:

Al(OH)$_3$ obtained by hydrolysis of aluminum triisopropylate and deposited on a kieselguhr base obtained from Merck and Company. The weight ratio of Al(OH)$_3$ to support was 1:2. The catalyst was identified as catalyst a.

γ-Alumina Type F 1 of Alcoa Company in granular form (in the batch test described as follows, γ-alumina was used in pulverulent form). The γ-alumina catlayst in each instance is designated as catalyst b.

Copper chromite catalyst in pelleted form, Girdler Type G13. (Here also, the catalyst when used in batch test was in powder or pulverulent form). The copper chromite catalyst is designated in each instance as catalyst c.

Several different comparative tests involving the Alfol mixtures and the catalysts above described were conducted. The diol contents of the various alcohols mixtures were determined. The diol content was determied by thin layer chromatography, using glass plates coated with silica gel. The solvent for the sample was tetrahydrofuran, the mobile phase consisted of a solvent of acetic acid ethyl ester and hexane and after evaporation of the solvent oleum containing 15% $SO_3$ was used as the color development agent. The oleum was at a temperature of 180°C. 1,12-dodecane diol in graded concentrations was applied as the gauge substance on each of the plates, together with the samples. The qualitative correlation of the diols contained in the samples was performed by comparing their $R_F$ values (rates of flow) with those of the gauge substance. The quantitative analysis was performed by associating the degrees of blackness of the sample diol spots to the spots of the gauge substance.

Hydroxyl number determinations were also performed on the various alcohols. The alcohol content in the reaction mixtures was determined by acetylation with excess acetic acid anhydride and acidimetric titration of the formed acetic acid according to Deutsche Gesellschaft für Fettwissenschaft standard method C V 17 a. The results are given in grams potassium hydroxide per milligram of substance.

Bromine determinations were also made of the unsaturated components. Here, the existing and the newly formed olefinic double bonds were measured. The determination was carried out by the addition of bromine according to Deutsche Industrie Norm 51 774, corresponding to ASTM D 1158. The results given are given in grams of $Br_2$ per 100 grams of substance.

Several of the experiments were conducted employing an aluminum hydroxide catalyst. Referring to Table 1 below, catalyst a, the aluminum hydroxide catalyst, and catalyst b, the γ-alumina catalyst, were evaluated for their ability to selectively dehydrate the secondary hydroxyl group of the Alfol A mixture, 1,12-octadecane diol. The process was conducted in two stages. A first dehydration was carried out for 1 hour at 220°C. A subsequent dehydration was carried out using in two instances 300°C for 2.75 hours and in the other instance 220°C for 2.75 hours. The results are summarized in Table 1.

From the foregoing and the showings in Table 1 it is clear that the alumina trihydroxide catalyst does not provide selective dehydration of the diols, whereas when the catalyst was γ-alumina the diol content was reduced to less than 0.1 weight percent.

The end product obtained from the attempted dehydration with catalyst a on Alfol mixture A was a solid wax-like product which still contained about 70% diol. The end product obtained when the second stage was incrased to 320°C (using aluminum trihydroxide as the catalyst) was an oily slightly yellowish product. Considerable dehydration of primary hydroxyl groups was experienced, forming especially primary-secondary and primary-primary ethers as revealed by infra-red, nuclear magnetic resonance and gas chromatography analyses, the latter being performed in silylized samples. The process was by no means a selective dehydration favoring removal of the secondary hydroxyl groups.

Another series of experiments were conducted using catalysts $a$ and $b$ and Alfol mixture B. In this series of experiments a fine pulverulent catalyst was employed and 100 grams of Alfol B mixture. The catalyst and Alfol mixture was filled into a 250 ml four-neck glass flask equipped with water separator, gas inlet tube, sampling tube and propellant mixture. The charge was heated with a moderate stream of gas using nitrogen gas within a heating jacket to the indicated temperatures. The mixing speed was 400 to 450 RPM, thereby obtaining a uniform suspension of the catalyst powder in the liquid reaction mixture.

Intermediate samples and end product samples were obtained which were immediately filtered with suction through a sintered glass plug so as to separate the suspended catalyst therefrom. At room temperature, the filtrate congealed to a waxy solid. All tests carried out in this series were performed without pressure. The conditions and results of the comparative tests are set forth in Table 2 below. The "%OHN loss" was determined by the following equation:

$$\frac{(OHN_{Initial} - OHN_{End}) \times 100}{OHN_{Initial}} = \% \text{ OHN loss}$$

When dehydration of the secondary OH groups is complete and 100% selective, the numerical value is slightly smaller than that of the percent diol in the charge mixture.

There is thus shown not only that catalyst $b$ is far superior to catalyst $a$, but also that catalyst $a$ is by no means suitable for the selective dehydration of secondary hydroxyl groups in diols, because the desired ratio between activity and selectivity is, for this catalyst, far too low.

TABLE 1

| Run No. | Alfol Mixture | Catalyst type | wt.% | Temperature/Time 1st stage | 2nd stage | Data of End Products % diol | OHN | BrN |
|---|---|---|---|---|---|---|---|---|
| I/1 | A | a | 2.5 | 220°C/1 hr. | 300°C/2.75 hrs. | 70 | 318 | 11.7 |
| I/2 | A | a | 2.5 | 220°C/1 hr. | 320°C/2.75 hrs. | 6 | 131 | 45.6 |
| I/3 | A | b | 2.5 | 220°C/1 hr. | 300°C/2.75 hrs. | 0.1 | 85 | 66 |
| Theoretical values for octadecenol: | | | | | | | 209 | 60 |

TABLE 2

| Run No. | Alfol Mixture | Catalyst type | wt.% | Temperature °C | Time Hours | Data of % diol | OHN | End Products BrN | %OHN loss |
|---|---|---|---|---|---|---|---|---|---|
| II/1 | B | b | 3 | 220 | 3 | 0.05 | 272 | 0.56 | 1.2 |
|  |  |  |  |  | 5 | 0.03 | 271 | 0.60 | 1.5 |
| II/2 | B | b | 5 | 220 | 5 | 0.02 | 270 | 0.68 | 1.8 |
| II/3 | B | a | 3 | 220 | 4 | 0.8 | 272 | 0.50 | 1.2 |
|  |  |  |  |  | 6 | 0.7 | 270 | 0.53 | 1.8 |
| II/4 | B | a | 5 | 220 | 4 | 0.6 | 269 | 0.53 | 2.2 |
|  |  |  |  |  | 8 | 0.5 | 268 | 0.59 | 2.5 |
| II/5 | B | a | 5 | 250 | 6 | 0.4 | 261 | 0.67 | 5.1 |
|  |  |  |  |  | 10 | 0.2 | 260 | 0.80 | 5.4 |
|  |  |  |  |  | 20 | 0.05 | 253 | 0.92 | 8.0 |

EXAMPLE 6

Another series of comparative experiments were performed to evaluate catalysts $b$ and $c$ against each other under the conditions of the present invention and under the conditions of U.S. Pat. No. 3,468,965 (Examples IX and XV). In these experiments, the results of which are reported in Table 3, a 200 ml V4A stainless steel autoclave equipped with a strong magnetic stirrer was filled with 50 grams of Alfol mixture C and the designated catalyst. The autoclave was flushed with nitrogen gas and thereafter with hydrogen. Subsequently, hydrogen gas was introduced under pressure at ambient temperature so that the heating was effected already under pressure. After reaching the reaction temperature, desired pressure is adjusted by introducing additonal hydrogen. The pressure was maintained during the test period as indicated in Table 3 below. The first experiment represents the conditions called for in Example IX of U.S. Pat. No. 3,468,965, while the second experiment reported in Table 3 represents the process parameters of Example XV of U.S. Pat. No. 3,468,965. The conditions and results are set forth in the table, indicating only the diol concentrations, hydroxyl numbers and hydroxyl number loss in percent, since these values sufficiently characterize activity and selectively of the catalysts and procedures.

TABLE 3

| Run No. | Alfol Mixture | Catalyst type | wt.% | Gas | Pressure Atmosph. Gauge | Temp. °C | Time | Data of End Products % diol | OHN | %OHN loss |
|---|---|---|---|---|---|---|---|---|---|---|
| III/1 | C | c | 0.5 | $H_2$ | 35 | 180 | 1.5 | 0.15 | 277 | 2.5 |
| III/2 | C | c | 1.0 | $H_2$ | 7 | 200 | 0.66 | 0.12 | 277 | 2.5 |
| III/3 | C | c | 10.0 | $H_2$ | 0 | 190 | 6 | 0.08 | 233 | 17.9 |
| III/4 | C | c | 10.0 | $N_2$ | 0 | 190 | 6 | 0.12 | 229 | 19.4 |
| III/5 | C | b | 10.0 | $N_2$ | 0 | 190 | 6 | 0.02 | 276 | 2.8 |
| III/6 | C | b | 10.0 | $H_2$ | 0 | 190 | 6 | 0.02 | 276 | 2.8 |

The data shows that in the absence of pressure, catalyst $b$ provides a far superior reduction in diol concentration. Whereas in both instances, i.e., under a blanket of nitrogen or hydrogen, catalyst $b$ reduced the diol concentration to 0.02 weight percent, the best reduction could be obtained by catalyst c, the copper chromite on alumina catalyst, only when employing hydrogen. Still, the diol concentration was four times that of both the experiments wherein the catalyst was simply γ-alumina. Moreover, in the presence of hydrogen or nitrogen at atmospheric pressure, a copper chromite catalyst does not behave selectively and effects a marked reduction of over-all hydroxyl content, indicating a substantial dehydration of primary monoalcohol groups. The data in Table 3 also showed that even when under conditions of super-atmospheric pressure, catalyst c effects some selective dehydration, the catalyst is still far less effective than the γ-alumina catalyst. In fact, the selectivity obtained by catalyst c is obtained, in the case of the experiments paralleling Examples IX and XV of U.S. Pat. No. 3,468,965 only at the expense of lesser activity in respect of diol dehydration. Thus, catalyst c dehydrates more diol at atmospheric pressure, but also dehydrates terminal hydroxyl groups. To eliminate this dehydration of terminal hydroxyl groups, pressure is employed, which pressure decreases the activity of the catalyst over-all.

EXAMPLE 7

A further series of comparative tests with catalysts a, b and c was conducted to observe the behavior of these catalysts in a continuous dehydration process. In these series of experiments, Alfol mixture D was employed. A V4A stainless steel reactor tube of 22.5 mm inside diameter and 250 mm effective height, equipped with an electric heating jacket, connections for feeding gas and liquid product at the bottom of the reactor and a thermocouple as well as a pressureconstant product discharge means at the top of the reactor was employed. The same was filled with 100 ml of catalyst which was confined by close-meshed sieves in the tube.

The reactor was heated to the designated reaction temperature. The reactor was flushed with nitrogen or hydrogen gas as indicated and optionally pressured to operating pressure. One run for each catalyst was performed utilizing a super-atmospheric pressure of 7 atmospheres gauge. Pressure was supplied by hydrogen.

Thereafter, while maintaining the pressure (or a moderate stream of gas at 2 liters per hour in the test carried out at normal atmospheric pressure) 80 ml of liquid Alfol D mixture, preheated to 70°–80°C, was introduced into the reactor by means of a dosing pump. After filling the free reactor volume, the corresponding amount of reaction product was discharged. Part of the reaction water was removed already during the depressuring and along with the gas stream. The remainder was removed by phase separation after cooling the product to 90°C. The minimum reaction time was 10 hours. The liquid was passed through the reactor at a rate of 0.8 LHSV. Intermediate samples of product were taken after 5 hours of reaction. These showed practically the same results so that the state after 10 hours of reaction in any case was stationary.

In the tests, each of the catalyst a, b, and c was subjected to three tests, i.e., a run under normal pressure with nitrogen, a run under normal pressure with hydrogen and a run under 7 atmospheres gauge pressure with hydrogen. An additional run with catalyst b was carried out at 5 atmopsheres $H_2$ and 220°C. The results are set forth in Table 4 below. From the data, it is clear that catalyst a does not show any appreciable dehydration activity either at normal or under elevated pressure. While the hydroxyl number loss is very low, the diol itself is not removed to any appreciable extent.

On the other hand, using catalyst b, the diol content is reduced to 0.02 weight percent. Although it is true that to obtain such a good degree of diol removal one has to accept a 2.5 to 3% loss of primary hydroxyl groups, such loss is not appreciable when compared to the benefits derived by such marked reduction in diol content. Since this loss results mainly from the formation of ethers which occur as "dimers", mainly in the $C_{20+}$ fraction, Alfol cuts up to $C_{18}$ Alfols are contaminated only to a very small extent.

Catalyst c shows certain activity when hydrogen gas is used as the gas phase and exhibits a markedly better selectivity at lower pressures, e.g. atmospheric pressure. This is in contrast to the statements made in U.S. Pat. No. 3,468,965 recommending pressures in excess of 100 psig. However, the resultant residual diol content is still too insubstantial. With nitrogen gas as the gas phase, the activity and selectivity of catalyst c are lower.

TABLE 4

| Run No. | Alfol Mixture | Catalyst | Gas | Pressure Atmosph. Gauge | Temp. °C | SV[1] | Data of End Products | | |
|---|---|---|---|---|---|---|---|---|---|
| | | | | | | | % Diol | OHN | %OHN loss |
| IV/1 | D | a | $N_2$ | 0 | 195 | 0.8 | 0.35 | 326 | 1.2 |
| IV/2 | D | a | $H_2$ | 0 | 195 | 0.8 | 0.35 | 327 | 1.1 |
| IV/3 | D | a | $H_2$ | 7 | 195 | 0.8 | 0.4 | 329 | <1.0 |
| IV/4 | D | b | $N_2$ | 0 | 195 | 0.8 | 0.02 | 320 | 3.0 |
| IV/5 | D | b | $H_2$ | 0 | 195 | 0.8 | 0.02 | 318 | 3.6 |
| IV/6 | D | b | $H_2$ | 7 | 195 | 0.8 | 0.30 | 328 | <1.0 |
| IV/6a | D | b | $H_2$ | 5 | 220 | 0.5 | 0.03 | 320 | 3.0 |
| IV/7 | D | c | $N_2$ | 0 | 195 | 0.8 | 0.12 | 307 | 7.0 |
| IV/8 | D | c | $H_2$ | 0 | 195 | 0.8 | 0.08 | 325 | 1.5 |
| IV/9 | D | c | $H_2$ | 7 | 195 | 0.8 | 0.10 | 315 | 4.5 |

[1]SV = space velocity (ml Alfol/ml catalyst/hour)

The above data show that such process can be carried out using either nitrogen or hydrogen as the gas phase substantially without deleterious effects. Moreover, said data demonstrate superior diol dehydration by the use of γ-alumina as the catalyst, particularly with the lower pressure. Elevating said pressure generally leads to some loss in activity of all catalysts. As is shown by Run IV/6a, however, activity and selectivity characteristics of catalyst b in Run 5 may be essentially restored, if the temperature is increased and the space velocity is reduced.

What is claimed is:

1. A process for selectively converting a secondary alkanediol in admixture with a primary monoalkanol to a primary monoalcohol without appreciably effecting dehydration of said primary monoalkenol, which comprises passing a mixture of secondary alkanediol and primary monoalkanol at a temperature of from about 170° to 220°C in the liquid phase over a dehydrating agent consisting essentially of a gamma-alumina catalyst.

2. A process according to claim 1 wherein said diol is $C_6$–$C_{12}$ aliphatic diols, said monoalcohols is $C_4$–$C_{20}$ monoalkanol and said diols are present in the diol-monoalkanol feed in an amount between 0.4 and 1.4% by weight.

3. A process according to claim 2 wherein the process is carried out at atmospheric pressure.

4. A process according to claim 3 wherein the process is carried out in the presence of hydrogen gas.

5. A process according to claim 3 wherein the process is carried out in the presence of nitrogen gas.

6. A process according to claim 2 wherein the diol-monoalkanol feed is maintained as it passes over said γ-alumina catalyst under a hydrogen gas atmosphere at a hydrogen pressure up to 10 atmospheres absolute.

7. A process according to claim 2 wherein the diol-monoalkanol feed is maintained as it passes over the γ-alumina catalyst in a gaseous atmosphere consisting essentially of nitrogen at a nitrogen pressure up to 10 atmospheres absolute.

8. A process according to claim 6 wherein the pressure is less than 6.5 atmospheres absolute.

9. A process according to claim 7 wherein the pressure is less than 6.5 atmospheres absolute.

10. A process according to claim 2 wherein said diols are straight or branch chain diols having one terminal hydroxyl group.

11. A process according to claim 2 wherein a major amount of said monoalcohols is $C_{10}$–$C_{12}$ straight chain monoalcohols.

12. A process according to claim 1 wherein said diol is $C_8$–$C_{14}$ aliphatic diols.

13. A process according to claim 2 wherein said mixture is maintained in contact with said γ-alumina for a period between 3 and 8 hours.

14. A process according to claim 2 wherein said mixture is continuously passed over said γ-alumina at an LHSV of between 0.5 and 1.5.

15. A process according to claim 1 wherein the product resulting from dehydration of said secondary diol is thereafter subjected to hydrogenation to hydrogenate double bonds contained in the so-formed monoalcohol.

16. A process according to claim 6 wherein the hydrogen pressure is 1 to 5 atmospheres absolute.

17. A process according to claim 7 wherein the nitrogen pressure is 1 to 5 atmospheres absolute.

* * * * *

UNITED STATES PATENT AND TRADEMARK OFFICE
CERTIFICATE OF CORRECTION

PATENT NO. : 3,966,829
DATED : June 29, 1976
INVENTOR(S) : Friedrich Engelhardt et al It is certified that error appears in the above-identified patent and that said Letters Patent are hereby corrected as shown below:

Column 5, line 67

"catlayst" should be "catalyst".

Column 11, line 6 (claim 2)

"monoalcohols" should be "monoalkanol".

Signed and Sealed this

Twelfth Day of October 1976

[SEAL]

Attest:

RUTH C. MASON
Attesting Officer

C. MARSHALL DANN
Commissioner of Patents and Trademarks